United States Patent

Kim et al.

(10) Patent No.: US 7,745,620 B2
(45) Date of Patent: Jun. 29, 2010

(54) DISUBSTITUTED CUCURBITURILS AND PREPARING METHOD THEREOF

(75) Inventors: Kimoon Kim, Pohang (KR); Jae Wook Lee, Pohang (KR); Dong Hyun Oh, Pohang (KR); Jeongmin Ju, Pohang (KR)

(73) Assignee: Postech Foundation, Pohang (KR)

( * ) Notice: Subject to any disclaimer, the term of this patent is extended or adjusted under 35 U.S.C. 154(b) by 610 days.

(21) Appl. No.: 10/598,861

(22) PCT Filed: Mar. 13, 2004

(86) PCT No.: PCT/KR2004/000536

§ 371 (c)(1),
(2), (4) Date: Sep. 13, 2006

(87) PCT Pub. No.: WO2005/087777

PCT Pub. Date: Sep. 22, 2005

(65) Prior Publication Data

US 2008/0139821 A1   Jun. 12, 2008

(51) Int. Cl.
*C07D 257/10* (2006.01)
*C07D 235/02* (2006.01)
(52) U.S. Cl. .................... 540/472; 548/303.4
(58) Field of Classification Search ........... 540/472; 548/303.4
See application file for complete search history.

(56) References Cited

U.S. PATENT DOCUMENTS 6,365,734 B1 * 4/2002 Kim et al. .................. 540/460
7,388,099 B2 * 6/2008 Kim et al. ................. 548/305.4

FOREIGN PATENT DOCUMENTS

| DE | 19603377 A1 | 8/1997 |
| KR | 1020040069814 A | 8/2004 |
| WO | 00/68232 A1 | 11/2000 |
| WO | 03/004500 A1 | 1/2003 |
| WO | 03/055888 A1 | 7/2003 |
| WO | WO 03/55888 A1 * | 7/2003 |

OTHER PUBLICATIONS

Anthony Flinn, et al., "Decamethylcucurbit[5]uril", Angew. Chem. Int. Ed. Engl.1992, pp. 1475-1477, vol. 31, No. 11.
W. A. Freeman, et al., "Cucurbituril", Journal of American Chemical Society Journal, 1981, pp. 7367-7368, vol. 103.
Jaheon Kim, et al., "New Cucurbituril Homologues: Syntheses, Isolation, Characterization, and X-ray Crystal Structures of Cucurbit[n]uril (n=5, 7, and 8)", Journal of American Chemical Society Journal, 2000, pp. 540-541, vol. 122.

* cited by examiner

*Primary Examiner*—Joseph R Kosack
(74) *Attorney, Agent, or Firm*—Rothwell, Figg, Ernst & Manbeck, pc

(57) ABSTRACT

Provided are a disubstituted cucurbituril that can be easily substituted by a substituent according to a desired usage and a method for preparing the same. The disubstituted cucurbituril has two end functional groups that can covalently bind with a solid substrate or a biochemically useful compound to obtain a cucurbituril-bonded substrate, which enables application of the disubstituted cucurbituril as column packing materials for chromatography, additives to gas separation membranes, catalysts for various chemical reactions, chemical sensors, or biological sensors.

2 Claims, No Drawings

DISUBSTITUTED CUCURBITURILS AND PREPARING METHOD THEREOF

CROSS REFERENCE TO RELATED APPLICATION

This application is a 35 U.S.C. §371 National Phase Entry Application from PCT/KR2004/000536, filed Mar. 13, 2004, and designating the U.S.

FIELD OF THE INVENTION

The present invention relates to a disubstituted cucurbituril and a method for preparing the same. More particularly, the present invention relates to a disubstituted cucurbituril that can easily introduce substituents according to a desired usage and a method for preparing the same.

DESCRIPTION OF THE RELATED ART

W. Mock and coworkers characterized cucurbit[6]uril as a hexameric macrocyclic compound with the composition of C36H36N24O12 which was confirmed by X-ray crystal structure determination (J. Am. Chem. Soc. 1981, 103, 7367). They named it cucurbit[6]uril. Since then, an improved synthetic method of cucurbit[6]uril has been disclosed (DE 196 03 377 A1).

In early 2000, Kimoon Kim and coworkers reported the improved preparation and separation of the well-known cucurbit[6]uril and its homologues, cucurbit[n]urils (n=5, 7, 8) and identified their X-ray crystal structures (J. Am. Chem. Soc. 2000, 122, 540).

The above-described cucurbiturils are compounds comprising unsubstituted glycoluril monomer units.

Meanwhile, decamethylcucurbit[5]uril comprising substituted glycoluril monomer units was known (Angew. Chem. Int. Ed. Engl. 1992, 31, 1475).

However, introduction of an additional functional group into the decamethylcucurbit[5]uril by substitution is difficult, which renders cucurbiturils less practical.

SUMMARY OF THE INVENTION

Therefore, the present invention provides a disubstituted cucurbituril which can be easily substituted by a substituent according to its usage.

The present invention also provides a method for preparing a disubstituted cucurbituril.

According to an aspect of the present invention, there is provided a disubstituted cucurbituril represented by the following Formula 1:

Formula 1

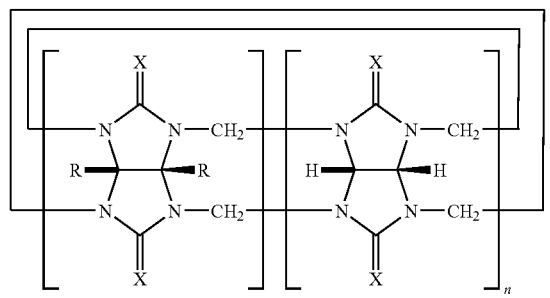

wherein
X is O, S, or NH;
n is an integer of 4 to 7;
R is selected from the group consisting of a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, a substituted or unsubstituted aminoalkyl group of C1-C30, a substituted or unsubstituted aryl group of C6-C30, and a substituted or unsubstituted heteroaryl group of C6-C30.

Preferably, R may be selected from the group consisting of a 2-nitrophenyl group, a 3-nitrophenyl group, a 4-nitrophenyl group, a 2-methoxyphenyl group, a 3-methoxyphenyl group, a 4-methoxyphenyl group, a 2-aminophenyl group, a 3-aminophenyl group, a 4-aminophenyl group, a 2-hydroxyphenyl group, a 3-hydroxyphenyl group, and a 4-hydroxyphenyl group.

According to another aspect of the present invention, there is provided a method for preparing a disubstituted cucurbituril represented by the following Formula 1, comprising reacting a disubstituted glycoluril represented by Formula 2 and a glycoluril represented by Formula 3 with formaldehyde:

Formula 1

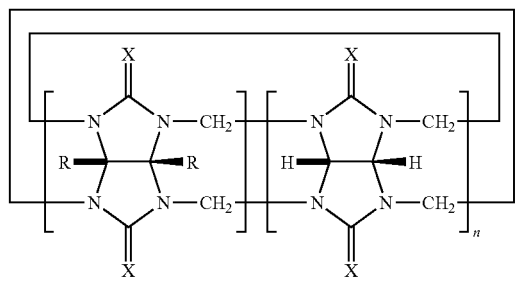

Formula 2

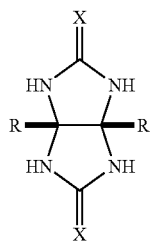

Formula 3

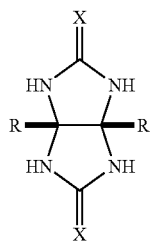

wherein
X is O, S, or NH;
n is an integer of 4 to 7;
R is selected from the group consisting of a substituted or unsubstituted alkenyl group of C2-C30, a substituted or unsubstituted alkynyl group of C2-C30, a substituted or unsubstituted alkylcarboxyl group of C2-C30, a substituted or unsubstituted hydroxyalkyl group of C1-C30, a substituted or unsubstituted alkoxy group of C1-C30, a substituted or unsubstituted nitroalkyl group of C1-C30, a substituted or unsubstituted aminoalkyl group of C1-C30, a substituted or unsubstituted aryl group of C6-C30, and a substituted or unsubstituted heteroaryl group of C6-C30.

The disubstituted glycoluril of Formula 2 may be prepared by reacting a 1,2-diketone derivative represented by Formula 4 with an urea represented by Formula 5 in the presence of an acid catalyst:

Formula 4

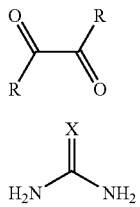

Formula 5 wherein X and R are as defined in the above.

The acid catalyst may be one or more selected from the group consisting of a hydrochloric acid, a sulfuric acid, and a trifluoroacetic acid.

In the reaction of the disubstituted glycoluril of Formula 2, the glycoluril of Formula 3, and the formaldehyde, the acid catalyst may be primarily added and stirred at 70-85° C. for 20-60 minutes and, when gelation occurs, the acid catalyst may be further added and stirred at 90-100° C. for 12-30 hours.

After the reaction of the disubstituted glycoluril of Formula 2, the glycoluril of Formula 3, and the formaldehyde is terminated, a reaction mixture may be left stand at room temperature for 1-20 hours and a cucurbituril precipitate may be filtrated to obtain a disubstituted cucurbituril-containing filtrate. One or more of acetone and methanol may be added to the filtrate to form a precipitate and the precipitate may be washed with a mixed solvent of acetone and water (2:1 to 10:1, by volume) to prepare the disubstituted cucurbituril of Formula 1.

The disubstituted cucurbituril of Formula 1 where R is an aminophenyl group may be prepared by reacting the disubstituted glycoluril of Formula 2 where R is a nitrophenyl group and the glycoluril of Formula 3 with the formaldehyde to form a disubstituted cucurbituril of Formula 1 where R is a nitrophenyl group, followed by reduction of the disubstituted cucurbituril.

The reduction may be carried out in the presence of one or more reducing agents selected from the group consisting of hydrogen, ammonium formate, tin and tin chloride, hydrazine, iron and iron chloride, zinc, formic acid, hydrogen sulfide, ammonia, sodium sulfide, titanium chloride, and aqueous ammonium sulfide solution.

The disubstituted cucurbituril of Formula 1 where R is a hydroxyphenyl group may be prepared by reacting the disubstituted glycoluril of Formula 2 where R is a methoxyphenyl group and the glycoluril of Formula 3 with the formaldehyde to form a disubstituted cucurbituril of Formula 1 where R is a methoxyphenyl group, followed by deprotection of the disubstituted cucurbituril.

The deprotection may be carried out in the presence of one or more selected from the group consisting of boron tribromide, boron trichloride, sodium alkyl sulfide, sodium sulfide, sodium cyanide, lithium iodide, aluminum bromide, 9-borobicyclo[3.3.1]nonane (9-BBN), pyridinium chloride salt, methyl magnesium iodide, hydrobromic acid, acetic acid, aluminum chloride, and lithium chloride.

DETAILED DESCRIPTION OF THE INVENTION

The present invention provides a disubstituted cucurbit[m]uril where m=n+1 and m is an integer of 5 to 8, represented by Formula 1:

Formula 1

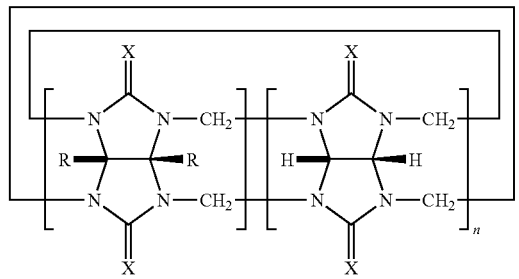

wherein X, n, and R are as defined in the above.

The term "heteroaryl" means an aromatic group having 6 to 30 ring atoms, which contains 1, 2 or 3 hetero atoms selected from N, O, P and S, and the remaining ring atoms of which are carbon. The term "heteroaryl" also means an aromatic group forming a quaternary salt or N-oxide which is obtained by oxydizing a heteroatom in the ring. Examples of such heteroaryl radicals include, but are not limited to, thienyl, benzothienyl, pyridinyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, and their equivalent N-oxides (e.g., pyridyl N-oxide or quinolinyl N-oxide), and quaternary salts thereof.

In Formula 1, one or more hydrogen atoms on the alkenyl group of C2-C30, the alkynyl group of C2-C30, the alkylcarboxyl group of C1-C30, the hydroxyalkyl group of C1-C30, the nitroalkyl group of C1-C30, the aminoalkyl group of C1-C30, the aryl group of C6-C30, and the heteroaryl group of C6-C30 may be substituted by a halogen atom, halide, a hydroxy group, a nitro group, an alkoxy group, a cyano group, a substituted or unsubstituted amino group, a carboxyl group, a sulfonic acid group, an alkyl group of C1-C10, or an aryl group of C6-C15.

A method for preparing the disubstituted cucurbituril of Formula 1 will now be described in detail.

First, a 1,2-diketone derivative of Formula 4 reacts with an urea of Formula 5 in the presence of an acid catalyst to obtain a disubstituted glycoluril of Formula 2:

Scheme 1

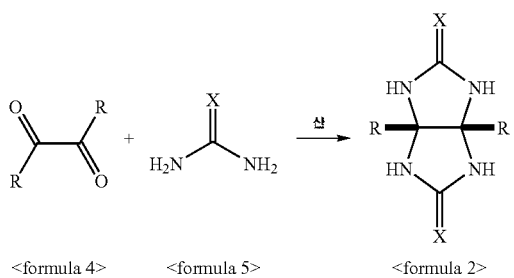

wherein X and R are as defined in the above.

In Scheme 1, the urea is used in an amount of 2 to 3 moles, based on 1 mole of the 1,2-diketone derivative. The acid catalyst is not particularly limited and may be hydrochloric acid, sulfuric acid, or trifluoroacetic acid. Hydrochloric acid is preferable. The acid catalyst is used in an amount of 0.4 to 3 moles, based on 1 mole of 1,2-diketone derivative.

The reaction temperature varies depending a kind of the 1,2-diketone derivative and the urea but may be in a range of 50 to 100° C.

Next, the disubstituted glycoluril of Formula 2 reacts with glycoluril of Formula 3 in the presence of a formaldehyde and an acid catalyst as the following Scheme 2:

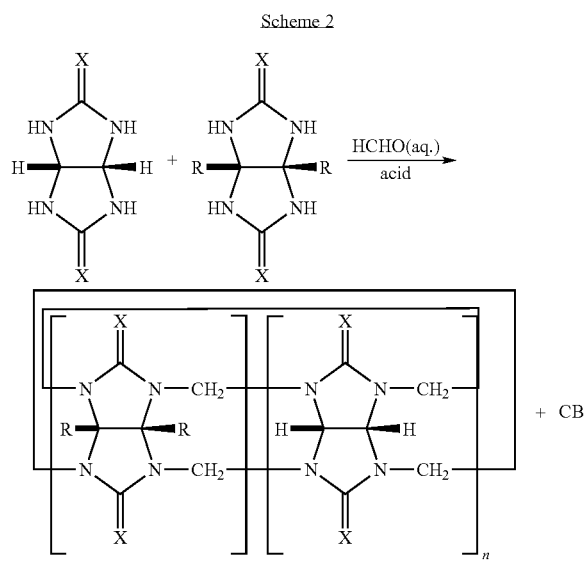

wherein X, R, and n are as defined in the above.

In Scheme 2, a disubstituted cucurbit[m]uril where m is an integer of 5-8 is synthesized by reacting the glycoluril of Formula 3 with the disubstituted glycoluril of Formula 2 in a molar ratio of n to 1.2 n (i.e., 4 to 7.2):1. For example, where m is 5 (n is 4), the glycoluril of Formula 3 reacts with 1 mole of the disubstituted glycoluril of Formula 2 in an amount of 5 to 5.2 moles. The acid catalyst may be hydrochloric acid, sulfuric acid, or trifluoroacetic acid. The formaldehyde may be used in an amount of 1 to 1.5 moles, based on 1 mole of the disubstituted glycoluril of Formula 2.

The acid catalyst is primarily added to a mixture of the disubstituted glycoluril of Formula 2 and the glycoluril of Formula 3 and stirred at 70-85° C. for 20-60 minutes. When gelation occurs, the acid catalyst is further added thereto and stirred at 90-100° C. for 12-30 hours.

After the reaction is terminated, the work-up of the resultant solution is carried out to obtain the disubstituted cucurbituril of Formula 1. The work-up method is not particularly limited and recrystallization using acetone and water may be preferably used. In detail, the reaction mixture is left stand at room temperature for 1 to 20 hours to obtain a cucurbituril precipitate and filtered. Then, acetone is added to a filtrate obtained to form a precipitate. The precipitate is several times washed with a mixed solvent of acetone and water (2:1 to 10:1, by volume) and dried to obtain the disubstituted cucurbituril of Formula 1 (yield 15-30%).

In the disubstituted cucurbituril synthesized by Scheme 2, when an end functional group of R is an alkenyl group, an alkynyl group, a hydroxy group, or an amino group, a covalent bond between the disubstituted cucurbituril and a substrate can be easily formed. However, the disubstituted cucurbituril where an end functional group of R is a nitro group or an alkoxy group is used after converting the nitro group and the alkoxy group to an amino group and a hydroxy group, respectively.

The disubstituted cucurbituril of Formula 1 where an end functional group of R is a nitro group is converted into the disubstituted cucurbituril of Formula 1 where an end functional group of R is an amino group by reduction. For example, diaminophenylcucurbituril of Formula 1 is synthesized by reduction of dinitrophenylcucurbituril. The reduction may be carried out in the presence of a reducing agent such as hydrogen, ammonium formate, tin and tin chloride, hydrazine, iron and iron chloride, zinc, formic acid, hydrogen sulfide, ammonia, sodium sulfide, and titanium chloride. An aqueous ammonium sulfide solution is preferred. The aqueous ammonium sulfide solution has advantages in that it solubilizes the dinitrophenylcucurbituril in an aqueous solution and excess ammonium sulfide is easily removed by sublimation after reaction termination.

The disubstituted cucurbituril of Formula 1 where an end functional group of R is an alkoxy group is converted into the disubstituted cucurbituril of Formula 1 where an end functional group of R is a hydroxy group by deprotection. For example, the dihydroxyphenylcucurbituril of Formula 1 is synthesized by deprotection of the dialkoxyphenylcucurbituril. The deprotection may be carried out in the presence of boron tribromide, boron trichloride, silane iodide, sodium alkyl sulfide, sodium sulfide, sodium cyanide, lithium iodide, aluminum bromide, 9-BBN, pyridinium chloride salt, methyl magnesium iodide, hydrobromic acid, acetic acid, aluminum chloride, and lithium chloride. Hydrobromic acid and acetic acid are preferred.

The disubstituted cucurbituril of Formula 1 covalently bonded with a solid substrate can be used in various applications. In more detail, the disubstituted cucurbituril of the present invention contains end functional groups reactive for addition or substitution reaction such as an unsaturated hydrocarbon, a hydroxy group, and an amino group. The end functional groups of the disubstituted cucurbituril covalently bind with end functional groups of a solid substrate to produce a cucurbituril-bonded substrate. The cucurbituril-bonded substrate can be used as packing materials of chromatographic columns, additives to gas separation membranes, or catalysts for various chemical reactions. According to a preferred embodiment of the present invention, there is provided a composite compound obtained by a covalent linkage between the disubstituted cucurbituril and a biochemical compound such as C60 and biotin. The composite compound binds with a specific substrate through a non-covalent bonding for various molecules, thereby promoting transfer and dissociation of biochemically important substances. The applications of the disubstituted cucurbituril of the present invention are now being extended to chemical sensors or biological sensors by a covalent linkage between the disubstituted cucurbituril and a surface of metal or glass or chromophore.

The disubstituted cucurbituril of the present invention can directly covalently bind with a specific substrate. Based on this fact, various applications and significance of the disubstituted cucurbituril can be understood. Further, it will be understood by those of ordinary skill in the art that various syntheses and applications of the disubstituted cucurbituril may be made without departing from the spirit and scope of the present invention as defined by the following claims.

Hereinafter, the present invention will be described more specifically by Synthesis Examples. However, the following Synthesis Examples are provided only for illustrations and thus the present invention is not limited to or by them.

Synthesis Example 1

Synthesis of di-meta-nitrophenyl glycoluril 1.7 g of di-meta-nitrobenzil, 1.7 g of urea, and 0.5 Ml of concentrated hydrochloric acid were mixed with 40 Ml of ethanol and refluxed using a Dean-Stark trap under a nitrogen gas atmosphere for 20 hours.

After the reaction was terminated, the reaction mixture was cooled to room temperature. An obtained solid was filtered and dried to give the di-meta-nitrophenyl glycoluril (yield 75%).

$^1$H-NMR (500 MHz, DMSO-$d_6$): δ 7.40 (t, J=5.0 Hz, 2H), 7.48 (d, J=5.0 Hz, 2H), 7.86 (s, 2H), 7.95 (d, J=5.0 Hz, 2H), 8.21 (s, 4H).

$^{13}$C-NMR (125 MHz, DMSO-$d_6$): δ 81.2, 121.6, 123.2, 129.7, 133.7, 140.5, 147.1, 160.2.

Synthesis Example 2

Synthesis of di-para-nitropheyl glycoluril

The di-para-nitrophenyl glycoluril (yield 91%) was synthesized in the same manner as in Synthesis Example 1 except that di-para-nitrobenzil was used instead of the di-meta-nitrobenzil.

$^1$H-NMR (500 MHz, DMSO-$d_6$): δ 7.37 (d, J=10.0 Hz, 4H), 7.97 (d, J=5.0 Hz, 4H), 8.17 (s, 4H).

$^{13}$C-NMR (125 MHz, DMSO-$d_6$): δ 81.3, 122.8, 128.7, 145.4, 147.1, 160.2.

Synthesis Example 3

Synthesis of di-para-methoxyphenyl glycoluril

The di-para-methoxyphenyl glycoluril (yield 88%) was synthesized in the same manner as in Synthesis Example 1 except that di-para-methoxybenzil was used instead of the di-meta-nitrobenzil.

$^1$H-NMR (500 MHz, DMSO-$d_6$): δ 3.71 (s, 6H), 6.95 (d, J=5.0 Hz, 4H), 7.28 (d, J=10.0 Hz, 4H), 7.76 (s, 4H).

$^{13}$C-NMR (125 MHz, DMSO-$d_6$): δ 55.4, 80.3, 112.8, 113.3, 115.9, 158.3, 163.4.

Synthesis Example 4

Synthesis of di-meta-nitrophenyl cucurbit[6]uril 3.84 g of the di-meta-nitrophenyl glycoluril of Synthesis Example 1, 7.14 g of glycoluril, 11.3 mL of a formaldehyde solution (37%), and 0.9 mL of concentrated hydrochloric acid were mixed and stirred at 80° C. for 30 minutes. The reaction mixture was cooled to room temperature. Then, 27 mL of concentrated sulfuric acid was gradually added at 0° C., stirred at 80° C. for 30 minutes, and cooled to 0° C. Then, 54 mL of water was gradually added and stirred at 95° C. for 24 hours.

After the reaction was terminated, the reaction mixture was left stand at room temperature for 3 hours and filtered through a filter to obtain a cucurbit[6]uril filtrate. Acetone was then added to the filtrate to obtain a precipitate and the precipitate was washed with acetone and water (5:1) to give the di-meta-nitrophenyl cucurbit[6]uril (yield 17%).

$^1$H-NMR (500 MHz, D$_2$O): δ 5.27 (d, J=10.0, 2H), 5.57 (d, J=10.0 Hz, 2H), 5.71 (m, 6H), 5.81 (m, 8H), 6.10 (m, 4H), 7.49 (m, 4H), 7.89 (d, J=25.0 Hz, 2H), 8.03 (m, 2H).

Synthesis Example 5

Synthesis of di-para-nitrophenyl cucurbit[6]uril

The di-para-nitrophenyl cucurbit[6]uril (yield 22%) was synthesized in the same manner as in Synthesis Example 4 except that the di-para-nitrophenyl glycoluril of Synthesis Example 2 was used instead of the di-meta-nitrophenyl glycoluril.

$^1$H-NMR (500 MHz, D$_2$O): δ 5.24 (d, J=10.0, 2H), 5.56 (d, J=5.0 Hz, 2H), 5.70 (m, 6H), 5.80 (m, 8H), 6.05 (d, J=15.0 Hz, 4H), 7.36 (d, J=5.0 Hz, 4H), 8.06 (d, J=10.0 Hz, 4H).

Synthesis Example 6

Synthesis of di-para-methoxyphenyl cucurbit[6]uril

The di-para-methoxyphenyl cucurbit[6]uril (yield 21%) was synthesized in the same manner as in Synthesis Example 4 except that the di-para-methoxyphenyl glycoluril of Synthesis Example 3 was used instead of the di-meta-nitrophenyl glycoluril.

$^1$H-NMR (500 MHz, D$_2$O): δ 3.71 (s, 6H), 4.38 (m, 12H), 5.24 (d, J=10.0, 2H), 5.56 (d, J=5.0 Hz, 2H), 5.70 (m, 6H), 5.80 (m, 8H), 6.05 (d, J=15.0 Hz, 4H), 7.11 (d, J=10.0 Hz, 4H), 7.43 (d, J=5.0 Hz, 4H).

Synthesis Example 7

Synthesis of di-meta-aminophenyl cucurbit[6]uril 380 mg of the di-meta-nitrophenyl cucurbit[6]uril of Synthesis Example 4 was dissolved in 3 mL of an aqueous 20% ammonium sulfide solution and stirred at room temperature for 20 minutes and then at 40° C. for 8 hours. A remaining ammonium sulfide was removed by heating at 80° C.

An obtained solid was filtered and dried to give the di-meta-aminophenyl cucurbit[6]uril (yield 84%).

$^1$H-NMR (500 MHz, D$_2$O): δ 5.27 (d, J=10.0, 2H), 5.56 (d, J=10.0 Hz, 2H), 5.70 (m, 6H), 5.80 (m, 8H), 5.97 (t, J=15.0 Hz, 4H), 6.26 (s, 2H), 6.39 (m, 2H), 6.62 (m, 2H), 7.04 (m, 2H).

Synthesis Example 8

Synthesis of di-para-aminophenyl cucurbit[6]uril

The di-para-aminophenyl cucurbit[6]uril (yield 84%) was synthesized in the same manner as in Synthesis Example 7 except that the di-para-nitrophenyl cucurbit[6]uril of Synthesis Example 5 was used instead of the di-meta-nitrophenyl cucurbit[6]uril.

$^1$H-NMR (500 MHz, D$_2$O): δ 5.39 (d, J=10.0, 2H), 5.71 (d, J=10.0 Hz, 2H), 5.85 (m, 6H), 5.94 (m, 8H), 6.10 (d, J=15.0 Hz, 4H), 6.75 (d, J=10.0 Hz, 4H), 6.85 (d, J=5.0 Hz, 4H).

Synthesis Example 9

Synthesis of di-para-hydroxyphenyl cucurbit[6]uril 200 mg of the di-para-methoxyphenyl cucurbit[6]uril of Synthesis Example 6 was dissolved in 10 mL of acetic acid and refluxed by addition of 0.2 mL of 47% hydrobromic acid. After 24 hours of the reaction, the resultant solution was cooled to room temperature and subjected to addition of acetone to obtain a precipitate. The precipitate was washed with water and acetone to give the di-para-hydroxyphenyl cucurbit[6]uril (yield 80%).

$^1$H-NMR (500 MHz, D$_2$O): δ 4.38 (m, 12H), 5.12 (m, 2H), 5.24 (d, J=10.0, 2H), 5.56 (d, J=5.0 Hz, 2H), 5.70 (m, 6H), 5.80 (m, 8H), 6.05 (d, J=15.0 Hz, 4H), 7.11 (d, J=10.0 Hz, 4H), 7.43 (d, J=5.0 Hz, 4H).

As apparent from the above descriptions, conventional cucurbiturils non-covalently bind with various types of compounds for molecular recognition. However, since such conventional cucurbiturils cannot be substituted by a substituent, they cannot bind with solid surfaces or biochemical compounds, which restricts various applications of cucurbiturils. Unlike the conventional cucurbiturils, the present invention provides a disubstituted cucurbituril that can be easily substituted by a substituent according to its utility and a method for preparing the same. Therefore, the disubstituted cucurbituril of the present invention can be easily covalently linked with desired biochemical compounds, solid surfaces, or solid substrates. Such a covalently bonded cucurbituril can be used in the fields of column packing materials for chromatographic columns, additives to gas separation membranes, catalysts for various chemical reactions, chemical sensors, or biological sensors.

What is claimed is:

1. A disubstituted cucurbit[m]uril where m is 5 to 8, represented by the following Formula I:

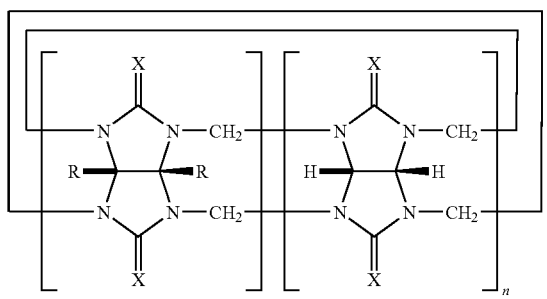

(1)

wherein n is an integer of 4 to 7;

X is O, S, or NH;

R is selected from the group consisting of a 2-nitrophenyl group, a 3-nitrophenyl group, a 4-nitrophenyl group, a 2-methoxyphenyl group, a 3-methoxyphenyl group, a 4-methoxyphenyl group, a 2-aminophenyl group, a 3-aminophenyl group, a 4-aminophenyl group, a 2-hydroxyphenyl group, a 3-hydroxyphenyl group, and a 4-hydroxyphenyl group.

2. A column packing material for chromatography comprising the disubstituted cucurbit[m]uril of claim 1.

* * * * *